US007745127B2

(12) United States Patent
Maes et al.

(10) Patent No.: US 7,745,127 B2
(45) Date of Patent: Jun. 29, 2010

(54) MOLECULAR DIAGNOSTIC METHOD FOR DEMENTIA WITH LEWY BODIES

(75) Inventors: Tamara Maes, Barcelona (ES); Carlos Buesa Arjol, Barcelona (ES); Marta Barrachina Castillo, Barcelona (ES); Isidro Ferrer Abizanda, Barcelona (ES)

(73) Assignee: Oryzon Genomics, S.A., Barcelona (ES)

( * ) Notice: Subject to any disclaimer, the term of this patent is extended or adjusted under 35 U.S.C. 154(b) by 413 days.

(21) Appl. No.: 11/658,057

(22) PCT Filed: Jul. 18, 2005

(86) PCT No.: PCT/EP2005/007813

§ 371 (c)(1),
(2), (4) Date: Apr. 9, 2007

(87) PCT Pub. No.: WO2006/008124

PCT Pub. Date: Jan. 26, 2006

(65) Prior Publication Data
US 2009/0028845 A1 Jan. 29, 2009

(30) Foreign Application Priority Data
Jul. 19, 2004 (ES) ............................... 200401764

(51) Int. Cl.
*C12Q 1/68* (2006.01)
*G01N 33/566* (2006.01)
*G01N 33/567* (2006.01)
(52) U.S. Cl. ........................ 435/6; 436/501; 436/503; 436/504
(58) Field of Classification Search ........................ None
See application file for complete search history.

(56) References Cited

U.S. PATENT DOCUMENTS

| 2004/0014142 A1 | 1/2004 | VanMechelen et al. |
| 2004/0072261 A1 | 4/2004 | Kostanjevecki et al. |
| 2005/0176078 A1 | 8/2005 | Allsop et al. |

FOREIGN PATENT DOCUMENTS

| WO | WO 99/50300 | 10/1999 |
| WO | WO 03/069332 A2 | 8/2003 |
| WO | WO 2005/045034 A2 | 5/2005 |

OTHER PUBLICATIONS

Choi et al., 2004, J. Biol. Chem., vol. 279, No. 13, pp. 13256-13264.*
Ardley et al., UCH-L1 aggresome formation in response to proteasome impairment indicates a role in inclusion formation in Parkinson's disease, Journal of Neurochemistry, 2004, pp. 379-391, vol. 90.
Chung et al., Abstract, The role of the ubiquitin-proteasomal pathway in Parkinson's disease and other neurodegenerative disorders, Trends in Neurosciences, Nov. 2001, pp. S7-S14, vol. 24, No. 11 Suppl.
Lowe et al., Abstract. Ubiquitin carboxyl-terminal hydrolase (PGP 9.5) is selectively present in ubiquitinated inclusion bodies characteristic of human neurodegenerative diseases, Journal of Pathology, Jun. 1990, pp. 153-160, vol. 161(2), Great Britain.
Nishikawa et al., Abstract, Alterations of structure and hydrolase activity of parkinsonism-associated human ubiquitin carboxyl-terminal hydrolase L1 variants, Biochemical and Biophysical Research Communications, Apr. 25, 2003, pp. 176-183, vol. 304, No. 1.
Pirim, I, Abstract, Production of anti-polyubiquitin and anti-ubiquitin carboxyl terminal hydrolase antibodies and immunohistochemically assessment of them on brain sections of Alzheimer's disease and Lewy body disease, International Journal of Neuroscience, Jul. 1998, pp. 33-42, vol. 95, No. 1-2, USA.
Rampello et al., Abstract, Dementia with Lewy bodies: a review, Archives of Gerontology and Geriatrics, Jul. 2004, pp. 1-14, vol. 39, No. 1.
Vaughan et al., Genetics of Parkinsonism: a review, Annals of Human Genetics, Mar. 2001, pp. 111-126, vol. 65, No. 2.
Von Bohlen Und Halbach et al., Abstract, Genes, proteins, and neurotoxins involved in Parkinson's disease, Progress in Neurobiology, Jun. 2004, pp. 151-177, vol. 73, No. 3.
Choi et al., Oxidative Modifications and Down-regulation of Ubiquitin Carboxyl-terminal Hydrolase L1 Associated with Idiopathic Parkinson's and Alzheimer's Diseases, The Journal of Biological Chemistry, Mar. 26, 2004, pp. 13256-13264, vol. 279, No. 13, USA.
Saigoh et al., Intragenic deletion in the gene encoding ubiquitin carboxy-terminal hydrolase in gad mice, Nature America Inc., Sep. 1999, pp. 47-51, vol. 23.
Long et al., Stimulation of the murine Uchl1 gene promoter by the B-Myb transcription factor, Lung Cancer, 2003, pp. 9-21, vol. 42.
McNaught et al., Impairment of the ubiquitin-proteasome system causes dopaminergic cell death and inclusion body formation in ventral mesencephalic cultures, Journal of Neurochemistry, 2002, pp. 301-306, vol. 81.
Liu et al., The UCH-L1 Gene Encodes Two Opposing Enzymatic Activities that Affect alpha-Synuclein Degradation and Parkinson's Disease Susceptibility, Cell, 2002, pp. 209-218, vol. 111.
Ardley et al., UCH-L1 aggresome formation in response to proteasome impairment indicates a role in inclusion formation in Parkinson's disease, Journal of Neurochemistry, 2004, pp. 379-391, vol. 90.
MacDonald et al., Gadzooks! Nature genetics, Sep. 1999, pp. 10-11, vol. 23.
Leroy et al., The ubiquitin pathway in Parkinson's disease, Nature, Oct. 1, 1998, vol. 395.
Tran et al., Aggregates in neurodegenerative disease: crowds and power? TINS, 1999, pp. 194-197, vol. 22, No. 5.

(Continued)

Primary Examiner—Olga N Chernyshev
(74) Attorney, Agent, or Firm—TraskBritt

(57) ABSTRACT

The present invention describes methods of molecular diagnosis of a concrete form of a-synucleinopathy, the dementia with Lewy bodies (DLB), associated to the levels of ubiquitin carboxy-terminal hydrolase L1 (UCH-L1) or the alteration of its ubiquityl-ligase activity. It also refers to the use of compounds that permit the modification of the UCH-L1 levels or of the enzymatic activity of UCH-L1. This invention has application in the diagnosis and treatment of patients suffering from DLB.

1 Claim, 5 Drawing Sheets

OTHER PUBLICATIONS

Hashimoto et al., Transgenic Models of alpha-Synuclein Pathology, Past, Present, and Future, Annals New York Academy of Sciences, 2003, pp. 171-188.

Mermerian et al., Structure-activity relationship, kinetic mechanism, and selectivity for a new class of ubiquitin C-terminal hydrolase-L1 (UCH-L1) inhibitors, Bioorganic & Medicinal Chemistry Letters, 2007, pp. 3729-3732, vol. 17.

Lansbury Jr, P.T., Improving Synaptic Function in a Mouse Mode of AD, Cell, 2006, Aug. 25, 2006, pp. 655-657, vol. 126.

Bifsha et al., Altered gene expression in cells from patients with lysosomal storage disorders suggests impairment of the ubiquitin pathway, Cell Death and Differentiation, 2007, pp. 511-523, vol. 14.

Gong et al., Ubiquitin Hydrolase Uch-L1 Rescues Beta-Amyloid-Induced Decreases in Synaptic Function and Contextual Memory, Cell, Aug. 25, 2006, pp. 775-788, vol. 126.

Hutter et al., Lack of evidence for an association between UCHL1 S18Y and Parkinson's disease, European Journal of Neurology, 2008, pp. 134-139, vol. 15.

Healy et al., Abstract, UCHL-1 is not a Parkinson's disease susceptibility gene, Ann Neurol., Apr. 2006, pp. 627-633, vol. 59, No. 4.

Mohammad et al., Abstract, Byostatin 1 induces ubiquitin COOH-terminal hydrolase in acute lymphoblastic leukemia cells, Enzyme Protein, 1996, pp. 262-272, vol. 49, No. 5-6.

Aigner et al., Abstract, Ribozyme-targeting of a secreted FGF-binding protein (FGF-BP) inhibits proliferation of prostate cancer cells in vitro and in vivo, Oncogene, 2002, pp. 5733-5742, vol. 21, No. 37.

Redlined Set of Claims submitted in European copending case (EP05766758.6), Mar. 11, 2009.

U.S. Appl. No. 12/214,522, filed Jun. 18, 2008 Arjol et al. Method for the Analysis of Differential Expression in Colorectal Cancer.

U.S. Appl. No. 12/308,808, filed Dec. 19, 2008 Schwartz Navarro et al. Prognostic Methods in Colorectal Cancer.

U.S. Appl. No. 12/225,008, filed Feb. 19, 2009 Maes et al. Method for Analysing Nucleic Acids.

Ballard et al., Abstract, Simple Standardised Neuropsychological Assessments Aid in the Differential Diagnosis of Dementia with Lewy Bodies from Alzheimer's Disease and Vascular Dementia, Dement Geriatr Cogn Disord, 1999, pp. 104-108, vol. 10.

Barrachina et al., Abstract, Amyloid-β deposition in the cerebral cortex in Dementia with Lewy bodies is accompanied by a relative increase in AβPP mRNA isoforms containing the Kunitz protease inhibitor, Neurochemistry International, Feb. 2005, pp. 253-260, vol. 46, No. 3.

Iwanaga et al., Lewy body-type degeneration in cardiac plexus in Parkinson's and incidental Lewy body diseases, Neurology, 1999, pp. 1269, vol. 52.

McKeith et al., Consensus guidelines for the clinical and pathologic diagnosis of dementia with Lewy bodies (DLB): Report of the consortium on DLB international workshop, Neurology, 1996, pp. 1113-1124, vol. 47.

Taki et al., Significance of $^{123}$I-MIBG scintigraphy as a pathophysiological indicator in the assessment of Parkinson's disease and related disorders: It can be a specific marker for Lewy body disease, Annals of Nuclear Medicine, 2004, pp. 453-461, vol. 18, No. 6.

\* cited by examiner

MOLECULAR DIAGNOSTIC METHOD FOR DEMENTIA WITH LEWY BODIES

OBJECT OF THE INVENTION

The present invention refers to a molecular diagnostic method and treatment of the disease known as dementia with Lewy bodies, both in its pure and common forms, which can be used as diagnostic criterion of these dementias as well as in their prevention and treatment.

BACKGROUND OF THE INVENTION

In developed societies, aging of the population is leading to an increase in the number of patients suffering from dementia. Most of these individuals suffer from Alzheimer's disease (AD). Among the non AD dementias, dementia with Lewy bodies (DLB) is of high prevalence. DLB designates a clinical-pathological syndrome of dementia associated with the cortical and subcortical presence of Lewy bodies in varying degrees, such as diffuse Lewy body disease, senile dementia of the Lewy body type and also Lewy body variant of Alzheimer's disease. Clinical-pathological classification of this dysfunction, which has been named dementia with Lewy bodies (DLB) (I. G. McKeith, D. Galasko, and K. Kosaka, et al., Consensus guidelines for the clinical and pathological diagnosis of Dementia with Lewy bodies (DLB): report on the Consortium on DLB International Workshop Neurology 1996; 47:1113-24.2000; 54:1050-8) also take into account traits common with the characteristics of the AD and of the Parkinson's disease (PD). As a whole, clinical data of the disease may suggest the diagnosis of diffuse Lewy body disease, but there are no definitive diagnostic tests for this disease. Neuropathological examination is at present the only form of diagnosis since it shows pathognomonic alterations by their characteristics, localization and distribution intrinsic of the disease.

Neurological criteria of diagnosis take into account symptoms or nuclear signs. Thus, considered in the evaluation of the dementia with Lewy bodies are attentional, executive and visual-spatial deficits, often most severe, and short-term memory, relatively less severe, than in AD. In the evaluation of fluctuating cognition, a variable temporal course of altered levels of attention and consciousness and the lack of sundown syndrome is encountered. Other key symptoms are recurrent and elaborate visual hallucinations. Typically, these include animated subjects with a variable degree of penetration. In DLB, the spontaneous extrapyramidal signs are rigidity, bradikynesia and motor abnormality; tremor at rest is infrequent. Presence of clinical fluctuations from one day to the next or from one week to the next, especially at the beginning, are aspects that reinforce the diagnosis of DLB. One aspect that might improve the diagnostic sensitivity are criteria to define threshold and scale of the nuclear traits of extrapyramidal motor signs and of visual hallucinations. A further limitation of the current criteria is that characteristics suggestive for diagnosis are not explicitly included in the algorithm used to determine the possible or probable nature of the DLB. To achieve higher precision in diagnosis of DLB, it would be necessary to investigate the utility of the suggestive traits for the differential diagnosis and possible contributions of the sleep alterations (D. I. Kaufer, Dementia and Lewy bodies, *Rev. Neurol.* 2003 Jul. 16-31; 37(2):127-30, Review).

From a histopathological point of view, the differential signs for a diagnosis of DLB are the presence of Lewy bodies in the cortex and the brain stem, even though in some cases, Lewy neurites, cortical senile plaques, signs of tau pathology or spongiform changes are detected (K. A. Jellinger, Morphological substrates of mental dysfunction in Lewy body disease, an update, *J. Neurol. Transm. Suppl.* 59 (2000), pp. 185-21). As mentioned above, the characteristics of the lesions (Lewy bodies and neurites), its localization (in neurones neuronal processes) and its distribution (diffuse in the brain stem, amygdala, Meynert's basal nucleus and cerebral cortex) are specific of the disease.

A recent study indicates a clinical incidence of DLB of 26 cases per 100,000 per year, with a maximum rate for the interval of 80-84 years of 68.6 cases per 100,000 per year. This rate is lower than AD, which in a previous study was identified in 93 cases per 100,000 per year but higher than for the fronto-temporal dementia (FTD), is estimated in 14 cases per 100,000 per year. The same study detected a male predominance of the DLB described in the literature, with a percentage of males with DLB versus AD of 63.2% versus 23.1%. In this study, several methodological limitations have to be considered because it is a study with a clinical sample of patients that are not representative of the general population. Also, it has to be taken into account that the insufficient sensitivity of the current clinical criteria may lead to an underestimation of the actual rates. Incidence in the general population may be slightly higher (S. López-Pousa, J. Garre-Olmo, A. Turon-Estrada, E. Gelada-Batile, M. Lozano-Gallego, M. Hernandez-Ferrándiz, V. Morante-Muñoz, J. Peralta-Rodríguez, and M. M. Cruz-Reina, Incidencia clinica de la demencia por cuerpos de Lewy, *Rev. Neurol.* 2003; 36 (8):715-720).

The etiology of the disease and the molecular mechanisms of its progression are still unknown. However, the main histopathological feature of this disease, accumulation of Lewy bodies, has provided for some of the first clues or indications. Lewy bodies are protein deposits mainly formed by insoluble protein deposits of which the main components are α-synuclein, ubiquitin and ubiquitinated proteins. All of these are members of a subcellular system called UPS system (ubiquitin-proteasome) that is responsible for physiological degradation of defective or overabundant cytoplasmic proteins (A. Herschko and A. Ciechanover (1998), The ubiquitin system, *Annu. Rev. Biochem.* 67:425-479). Malfunctioning of this system has been described as one of the causes involved in the onset or development of certain neurodegenerative diseases such as AD, PD, Huntington's disease (HD), or Amyotrophic Lateral Sclerosis (ALS) (L. Petrucelli and T. M. Dawson, Mechanism of neurodegenerative disease: role of the ubiquitin proteasome system, *Ann. Med.* 2004; 36(4):315-20). (P. B. Tran and R. J. Miller, Aggregates in neurodegenerative disease: crowds and power? *Trends Neurosci.* 1999 May; 22(5):194-7.)

One of the elements of the UPS system (ubiquitin-proteasome) responsible for physiological degradation of defective cytoplasmic proteins is UCH-L1 (ubiquitin carboxy-terminal hydrolase L1), a thiol-protease responsible for the hydrolysis of the peptidic bonds of the protein complexes bound to the carboxyterminal glycine of ubiquitin that lead to regulated destruction of proteins in excess in the cell cytoplasm and releasing ubiquitin that remain available to bind new proteins to be eliminated. The correlation between UCH-L1 and parkinsonism had been described with the detection of a dominant mutation in a German family with a PD history. (E. Leroy, R. Boyer, G. Auburger, B. Leube, G. Ulm, E. Mezey, G. Harta, M. J. Brownstein, S. Jonnalagada, T. Chernova, A. Dehejia, C. Lavedan, T. Gasser, P. J. Steinbach, K. D. Wilkinson, and M. H. Polymeropoulos (1998), The ubiquitin pathway in Parkinson's disease, *Nature* 395:451-452). Mice defective in UCH-L1 display lower in vivo neuronal ubiquitin levels than wild-type counterparts. In cultured cells, overexpression of UCH-L1 led to an increase in the levels of free ubiquitin (H. Osaka, Y. L. Wang, K. Takada, S. Takizawa, R. Setsuie, H. Li, Y. Sato, K. Nishikawa, Y. J. Sun, M. Sakurai, T. Harada, Y. Hara, I. Kimura, S. Chiba, K. Namikawa, H. Kiyama, M. Noda, S. Aoki, and K. Wada (2003), Ubiquitin carboxy-terminal hydrolase L1 binds to and stabilizes monoubiquitin in neurons, *Hum. Mol. Genet.* 12:1945-1958). It has been demonstrated that UCH-L1 colocalizes with other proteins of the UPS system such as ubiquitylated proteins, HSP70, gamma-tubulin and, to a lesser extent, the 20S proteasome and the BiP chaperone (H. C. Ardley, G. B. Scott, S. A. Rose, N. G. Tan, and P. A. Robinson, UCH-L1 aggresome formation in response to proteasome impairment indicates a role in inclusion formation in Parkinson's disease, *J. Neurochem.* 2004 July; 90(2):379-91). Recently, it has been described as alterations in the oxidative state of UCH-L1 in sporadic AD and PD (J. Choi, A. I. Levey, S. T. Weintraub, H. D. Rees, M. Gearing, L. S. Chin, and L. Li (2004), Oxidation and down-regulation of ubiquitin carboxyl-terminal hydrolase L1 associated with idiopathic Parkinson's and Alzheimer's disease, *J. Bio. Chem.* 279:13256-13264).

Despite degradation and subcellular protein homeostasis, pathways such as the UPS system and the different proteins that participate in it has been proposed as a key player in the development of diseases such as PD or AD. These share a number of symptoms with the DLB. Causes and mode of progression of this dementia, the second most frequent cause of dementia after AD, are still unknown.

Therapeutic options available to DLB patients are unfortunately very limited, often consisting only in symptomatic treatment to control psychiatric and parkinsonian symptoms. However, anti-parkinsons medication that leads to amelioration in tremor and mobility loss often produces acute and notable worsenings, in some cases fatal, of hallucinatory symptoms and of the psychotic pattern. Also, the prescribed neuroleptic treatment for the psychiatric symptoms produce a notable worsening of the motor pattern. Depending on the pattern showed by the patient, acetyl-cholinesterase inhibitors, dopamine agonists, short- and medium-life benzodiazepines and antidepressants may be of limited help (L. Rampello, S. Cerasa, A. Alvano, V. V. Butta, R. Raffaele, I. Vecchio, T. Cavallaro, E. Cimino, T. Incognito, and F. Nicoletti, Dementia with Lewy bodies: a review, *Arch. Gerontol. Geriatr.* 2004 July-August; 39(1):1-14.)

Therefore, there is a need for identifying new genes involved in and/or mutations responsible for and/or markers of the dementia with Lewy bodies.

The identification of genes would allow selective molecular diagnosis with regard to other dementias and would allow the diagnosis to be included in common clinical practice.

At the same time, it would produce a significant saving in social and health costs associated to these types of dementias, which are severely incapacitating.

It would also permit adoption of new prognostic and therapeutic orientation criteria in the positive cases since it would permit application to more severe and/or personalized therapies to those cases where the parkinsonian character of the disease is established.

Finally, identification of this/these genes and of possible compounds that might alter its/their expression, delaying or stopping the progression of the disease, would not only permit a selective molecular diagnosis with regard to other dementias, but it would also allow design of selective therapies intended to inactivate those genes.

DESCRIPTION OF THE INVENTION

The present invention refers to a diagnostic method for the dementia with Lewy bodies (DLB) in patients with suspected onset of dementia, comprising analysis of a sample obtained from a patient to determine the expression level of the ubiquitin carboxy-terminal hydrolase L1 (UCH-L1) gene or the enzymatic activity of the protein encoded by this gene.

In particular, this sample can be RNA or protein and can be isolated from cells obtained by biopsy or any other extraction methods of neural tissue or any other extraction method of any other tissue or from biologic fluids such as cerebrospinal fluid, serum or urine.

The diagnostic method of the present invention additionally comprises detection by a PCR amplification, a SDA amplification or any other method of amplification of DNA that permits quantitative estimation of the UCH-L1 transcript levels.

Optionally, detection may be carried out by DNA biochips made with oligonucleotides deposited by any mechanism, by DNA biochips made with oligonucleotides synthesized in situ by photolithography or any other mechanism.

Detection can also be carried out by means of a detection by analysis of the amount of protein present by Western blot, by "protein-chip" using specific antibodies against UCH-L1 or by protein profiles obtained by mass spectrometry or by any other mechanism that permits a quantitative estimation of the UCH-L1 protein levels.

Optionally, detection may be carried out by direct or indirect analysis of enzymatic activities of UCH-L1, both in vitro or in vivo, comprising the hydrolytic activity of esters and amides of ubiquitin as well as the ubiquityl-ligase activity.

The detection can also be carried out by direct analysis and quantification of the protein encoded by the gene or fragments thereof.

Optionally, detection can be carried out by direct or indirect analysis of the product of the UCH-L1 ligase activity, i.e., the presence of dimerized or polymerized forms of polyubiquitinin.

On the other hand, an additional object of the present invention is to provide a method of analysis of compounds to identify therapeutic agents based on its aptitude to strengthen the UCH-L1 levels to stop or reverse progression of this kind of dementias. Compounds may be specific promoters of UCH-L1 gene transcription or specific inhibitors of the degradation of the protein encoded by the UCH-L1 gene.

A further objective of the present invention is the use of compounds to increase or accelerate the hydrolytic activity of the UCH-L1 enzyme in order to stop or reverse progression of this kind of dementias. These compounds may affect the maximum rate or the affinity of UCH-L1 for the peptidyl-ubiquitin esters or amides.

A further objective of the present invention is the use of compounds to eliminate or decrease the ligase activity of the enzyme UCH-L1 to stop or reverse progression of this kind of dementias. Such compounds may act competitively or non-competitively as specific inhibitors of the ubiquityl-ligase activity of the protein encoded by the gene.

On the other hand, an additional objective of the present invention is to provide a method for analysis of compounds with therapeutical potential in dementia with Lewy bodies based on the analysis of the variation of the hydrolytic activity of UCH-L1 in in vitro systems such as cell cultures and others.

An additional objective of the present invention is to provide a method for analysis of compounds with therapeutical potential in dementia with Lewy bodies based on the analysis of the variation of the ubiquityl-ligase activity of UCH-L1 in in vitro systems such as cell cultures and others.

An additional objective of the present invention is to provide a pharmaceutical compound based on sequence information such as antisense or RNA interference oligonucleotides or other based on the destabilization and elimination of the mRNA or of the mRNA produced by an allele that confers ligase activity and the lack of its translation into protein.

An additional objective of the present invention is to provide a pharmaceutical compound based on the information of the UCH-L1 gene or protein sequences such as specific antibodies that produce an increase of its enzymatic activity in terms of affinity or maximum rate when they bind the protein or of antisense or RNA interference oligonucleotides or other based on the destabilization and elimination of the mRNA or of the mRNA produced by an allele that confers interference or reduction in trans with regard to the allele with normal hydrolytic activity and the lack of its translation into protein.

The present invention stems from genomic scale gene expression analysis of 627 genes of heightened interest in cerebral cortex tissue of a series of patients suffering from dementia with Lewy bodies (DLB) using specific oligonucleotide DNA chips. Samples from patients suffering from DLB, both in its pure form or in the form known as common, which also shows some symptoms concomitant of Alzheimer's disease, were analyzed. Levels of mRNA of the UCH-L1 gene were decreased compared to controls, as well as in comparison to a group of patients suffering from Alzheimer's disease (AD) or from Parkinson's disease (PD). Data were confirmed by independent techniques such as quantification of mRNA by real-time PCR. The significance of this decrease in the mRNA levels was also confirmed regarding the general and specific degradation processes in which different mRNA species are involved in post-mortem tissues. Experiments where the same post-mortem sample was processed and the RNA obtained from tissue having been at room temperature for different times showed that UCH-L1 levels remained constant, compared to the constitutive or comparatively invariable transcripts such as β-actin.

It was also confirmed that the protein levels analyzed by Western blot using anti-UCH-L1-specific antibodies, were also decreased in the cerebral cortex in DLB, but not PD.

The decrease in the UCH-L1 mRNA and protein levels was statistically significant, compared to controls with confidence levels of 0.99 for the pure form of the DLB and 0.95 for the common form.

Dementia with Lewy bodies (DLB) is the second most frequent cause of dementia after Alzheimer's disease (AD). Histopathologically, it is characterized by an accumulation of hyaline bodies (the Lewy bodies) in certain nuclei of the cerebral tract, spinal cord and autonomous ganglia. Lewy bodies are also produced in PD and both (PD and DLB) are considered as α-synucleinopathies due to the accumulation of this protein in the Lewy bodies. Despite DLB showing some symptomatic similarities with PD, these two diseases display very different neurological patterns and the cerebral affectation is also different. Thus, for example, DLB shows affectation of the cortex, which is not seen in PD. Hallucinatory neurological pattern is not present in PD. The anti-PD symptom treatment in DLB patients very severely worsens the neurological disease pattern in these patients. There is a well-established clinical and neurological consensus that these two diseases are clearly distinct.

UCH-L1 is an enzyme involved in UPS system (ubiquitin-proteasome) which is responsible for the physiological degradation of defective, mutant or overabundant cytoplasmic proteins. UCH-L1 is a thiol-protease that catalyzes hydrolysis of the peptidic bonds of the protein complexes bound to the carboxyterminal glycine of ubiquitin. This leads to regulated degradation of targeted proteins and releases ubiquitin, which can bind to further protein targets.

In PD, which has some symptoms in common with DLB, but contrary to DLB, never affects the cortex, the possible importance of the ubiquitin system has already been noted. Parkin, a protein known to interact with ubiquitin, is mutated in some cases of hereditary PD (K. S. McNaught and C. W. Olanow (2003), Proteolytic stress: a unifying concept for the etiopathogenesis of Parkinson's disease, *Ann. Neurol.* 53:S73-84). UCH-L1 was also related to PD when it was discovered that there is a point mutation (I93M), which, with a certain degree of dominance, confers disease susceptibility (E. Leroy, R. Boyer, G. Auburger, B. Leube, G. Ulm, E. Mezey, G. Harta, M. J. Brownstein, S. Jonnalagada, T. Chernova, A. Dehejia, C. Lavedan, T. Gasser, P. J. Steinbach, K. D. Wilkinson, and M. H. Polymeropoulos (1998), The ubiquitin pathway in Parkinson's disease, *Nature* 395:451-452). In a collaborative study where 11 studies were performed at that time and 1970 cases of PD and 2224 non-related controls were analyzed, it was found that there is a statistically significant inverse association between the S18Y allele and the Parkinson's disease (odds ratio (OR) of 0.84 (95% confidence interval [CI], 0.73-0.95) and homozygots for the allelic variant (Y/Y vs S/S plus Y/S) showed an OR of 0.71 (95% CI, 0.57-0.88), which confirmed UCH-LI as a susceptibility gene for PD. (D. M. Maraganore, T. G. Lesnick, A. Elbaz, M.-C. Chartier-Harlin, T. Gasser, R. Kruger, N. Hattori, G. D. Mellick, A. Quattrone, J. Satoh, T. Toda, J. Wang, J. P. A. Ioannidis, M. Andrade, and W. A. Rocca, UCH-L1 Global Genetics Consortium: UCH-L1 is a Parkinson's disease susceptibility gene, *Ann. Neurol.* 55:512-521, 2004). Recently, it has also been described as a reduction of UCH-LI levels and the presence of certain oxidative modifications in Alzheimer's and idiopathic Parkinson's (J. Choi, A. I. Levey, S. T. Weintraub, H. D. Rees, M. Gearing, L. S. Chin, and L. Li (2004), Oxidative modifications and down-regulation of ubiquitin carboxyl-terminal hydrolase L1 associated with idiopathic Parkinson's and Alzheimer's disease, *J. Biol. Chem.* 279:13256-13264).

However, a possible link between the UCH-L1 levels and dementia with Lewy bodies has so far not been described. The present invention shows a clear correlation between reduced UCH-L1 mRNA and protein levels of the cerebral cortex in DLB patients versus controls. Moreover, experiments of the present invention show very clearly how the reduction of the UCH-L1 protein levels in patients suffering from DLB do not show concomitant decreases of other key proteins of the ubiquitin-proteasome complex such as 20SX and 20SY subunits, 19S complex and 11Sα subunit of the PA28 activator. This indicates a specific and selective role of the repression of the UCH-L1 levels in the pathological pattern of DLB in the cerebral cortex.

At present, patients with suspected DLB assessed using basic neurological techniques, mental deterioration is detected by early symptoms such as difficulties in problem solving and visual and spatial difficulties, as well as fluctuations in the cognitive function and the appearance of well-defined hallucinations. Later, the appearance of motoric symptoms constitutes the main features for a discriminatory diagnosis of DLB with regard to other dementias (I. G. McKeith, D. Galasko, K. Kosaka, E. K. Perry, D. W. Dickson, L. A.

Hansen, D. P. Salmon, J. Lowe, S. S. Mirra, E. J. Byrne, G. Lennox, N. P. Quinn, J. A. Edwardson, P. G. Ince, C. Bergeron, A. Burns, B. L. Miller, S. Lovestone, D. Collerton, E. N. Jansen, C. Ballard, R. A. Vos, G. K. Wilcock, K. A. Jellinger, and R. H. Perry (1996), Consensus guidelines for the clinical and pathologic diagnosis of dementia with Lewy bodies (DLB): Report of the consortium on DLB international workshop, *Neurology* 47:1113-1124; and I. G. McKeith, C. G. Ballard, R. H. Perry, P. G. Ince, J. T. O'Brien, D. Neill, K. Lowery, E. Jaros, R. Barber, P. Thompson, A. Swann, A. F. Fairbairn, and E. K. Perry, Prospective validation of consensus criteria for the diagnosis of dementia with Lewy bodies, *Neurology* 2000 Mar. 14; 54(5):1050-8). An early unequivocal diagnosis would give a therapeutic margin to reduce or stop the disease progression.

In accordance with the diagnostic method of the present invention, the analysis of DLB would be as follows: a patient with suspected onset of dementia and with a non-definitive clinical-familial evaluation would be diagnosed by microbiopsy and a quantification of UCH-L1 levels.

Another embodiment of the present invention is the use of an anti-DLB therapy specifically to modify the ability to regenerate the intracellular free ubiquitin pool through increase in UCH-L1 mRNA or protein levels or through modification of one or more of the enzymatic activities of UCH-L1.

Knowledge of the enzymatic activities of UCH-L1, a hydrolase activity that releases ubiquitin (C. N. Larsen, B. A. Krantz, and K. D. Wilkinson, Substrate specificity of de-ubiquitinating enzymes: ubiquitin C-terminal hydrolases, *Biochemistry* 1998, 37:3358-68; and C. N. Larsen, J. S. Price, and K. D. Wilkinson. Substrate binding and catalysis by ubiquitin C-terminal hydrolases: identification of two active site residues, *Biochemistry* 1996, 35:6735-44) and the ubiquityl-ligase activity (Y. Liu, L. Fallon, H. A. Lashuel, Z. Liu, and P. T. Lansbury (2002), The UCH-L1 gene encodes two opposing enzymatic activities that affect a-synuclein degradation and Parkinson's disease susceptibility, *Cell* 111:209-218) allows the design of methods for analysis of compounds and permits determination of the efficacy of molecules that interfere with the UCH-L1 activities in the desired way.

Anti-DLB therapy starts by determining decreased UCH-L1 levels in neural tissue or in cerebrospinal or peripheral fluids. Mice defective in UCH-L1 have decreased levels of free ubiquitin in neurons. Cultured cells and transgenic mouse models overexpressing UCH-L1 show an increase of the ubiquitin levels (H. Osaka, Y. L. Wang, K. Takada, S. Takizawa, R. Setsuie, H. Li, Y. Sato, K. Nishikawa, Y. J. Sun, M. Sakurai, T. Harada, Y. Hara, I. Kimura, S. Chiba, K. Namikawa, H. Kiyama, M. Noda, S. Aoki, and K. Wada (2003), Ubiquitin carboxy-terminal hydrolase L1 binds to and stabilizes monoubiquitin in neuron, *Hum. Mol. Genet.* 12:1945-1958). Moreover, colocalization of a-synuclein and ubiquitin in Lewy bodies and in Lewy neurites (K. S. McNaught and C. W. Olanow (2003), Proteolytic stress: a unifying concept for the etiopathogenesis of Parkinson's disease, *Ann. Neurol.* 53:S73-84; K. S. McNaught, C. Mytilineou, R. Jnobaptiste, J. Yabut, P. Shashidharan, P. Jennert, and C. W. Olanow (2002), Impairment of the ubiquitin-proteasome system causes dopaminergic cell death and inclusion of body formation in ventral mesencephalic cultures, *J. Neurochem.* 81:301-306), as well as evidence indicating that important components of the UPS complex are not decreased in DLB mainly due to a reduction in the UCH-L1 activity, make a very probable hypothesis that the ubiquitin-proteasome system is involved in the pathogenesis of PD and DLB.

Therefore, the establishment of the clear correlation between the UCH-L1 levels and the DLB disease permits consideration of a novel application of the technologies and compounds to increase active enzyme levels, to inactivate the ubiquityl-ligase activity or to activate the hydrolase activity. This application of technologies and/or active compounds may stall and/or cause regression of the disease since they increase the available free ubiquitin in the cellular cytoplasmic pool and, therefore, allow neurones to correctly catabolize proteins that have to be eliminated. This could result in a decrease in the concentration of α-synuclein and other proteins responsible for Lewy bodies.

An example of an approach of overexpression of UCH-L1 would be the insertion of a cassette encoding the S18Y form of UCH-L1, which has a reduced ubiquityl-ligase capacity, into an adenoviral or retroviral expression vector or any other kind of expression vector. This vector might be introduced through transplantation in neural stem cells of embryonic or adult origin (derived from the subventricular zone or others) carrying the expression vector. A similar approach might be the transplantation of stem cells encoding a transcription factor. Recently, it has been demonstrated that a transcription factor, B-Myb, which was identified due to its similarity with v-Myb, an avian retrovirus oncogene, which modulates the transition G1/S of the cell cycle (N. Nomura, M. Takahashi, and M. Matsui et al., Isolation of human cDNA clones of myb-related genes, a-myb and b-myb, *Nucleic Acids Res.* 16 (1988), pp. 11075-11089, published erratum appears in *Nucleic Acids Res.* 1989 February 11; 17(3):1282), can stimulate expression of UCH-L1, both in vitro and in vivo in rat lung (E. M. Long, M. A. Long, M. Tsirigotis, and D. A. Gray, Stimulation of the murine UCH-L1 gene promoter by the B-Myb transcription factor, *Lung Cancer* 2003 October; 42(1):9-21).

Another example in this sense might be to introduce mutant versions of UCH-LI with elevated hydrolytic activity.

A demonstrative example of this effect may be postulated with neural cell lines of the rat ventral mesencephal where inhibition of UCH-L1 produces a-synuclein aggregates and overexpression results in an increase in the amount of free ubiquitin.

Another experimental example was obtained with the SH-SY5Y neuroblastoma cell line where treatments with 5-100 microM of MPP+, the active metabolite of MPTP, induce apoptosis in SH-SY5Y cells in the four days following the treatment and, moreover, were found to overexpress a-synuclein that forms the Lewy aggregates characteristic of the DLB (C. Gomez-Santos, I. Ferrer, J. Reiriz, F. Vinals, M. Barrachina, and S. Ambrosio, MPP+ increases alpha-synuclein expression and ERK/MAP-kinase phosphorylation in human neuroblastoma SH-SY5Y cells, *Brain Res.* 2002 May 10; 935 (1-2):32-9).

A small sub set of dementias may also have a familial character, as has been described in one case of PD where a UCH-L1 mutation (the German mutation I93M) causes a 50% decrease of the hydrolytic activity (P. T. Lansbury and A. Brice (2002), Genetics of Parkinson's disease and biochemical studies of implicated gene products, *Curr. Opin. Genet. Dev.* 13:299-306). Some DLB subtypes also seem to show an autosomal dominance to a certain degree (A. J. Harding, A. Das, J. J. Kril, W. S. Brooks, D. Duffy and G. M. Halliday, Identification of families with cortical Lewy body disease, *Am. J. Med. Genet.* 2004 Jul. 1; 128B(1):118-22). The mutation of UCH-L1 I93M also shows certain dominance, although its penetrance is not absolute, so that phenomena of allelic compensation in trans has been postulated (Y. Liu, L. Fallon, H. A. Lashuel, Z. Liu, and P. T. Lansbury (2002), The UCH-L1 gene encodes two opposing enzymatic activities that affect a-synuclein degradation and Parkinson's disease susceptibility, *Cell* 111:209-218).

Chemical and immunological inhibition of enzyme activities has seen successful application, e.g., in oncology, for example, on beta-cathenin in colorectal cancer and BCR-ABL in chronic myeloid leukemia. These observations suggest that certain oncogenes might be susceptible of a disruption, causing the fall of the tumoral phenotype or allowing the efficiency of the combined standard treatment. Among mechanisms available for genetic disruption, small interference RNA (RNAi) is one of the most promising approaches. Initially discovered in petunia (C. Napoli, C. Lemieux, and R. Jorgensen (1990), Introduction of a chalcone synthase gene into Petunia results in reversible co-suppression of homologous genes in trans, *Plant Cell* 2:279-289), its molecular mechanism of action has been described (S. M. Hammond, A. A. Caudy, and G. J. Hannon (2001), Post-transcriptional Gene Silencing by Double-stranded ARN, *Nature Rev. Gen.* 2:110-119) and has provoked great expectations in its antitumoral applications (R. Kittler and F. Buchholz, RNA interference: gene silencing in the fast lane, *Semin. Cancer Biol.* 2003 August; 13(4):259-65; Q. L. Deveraux, P. Aza-Blanc, K. W. Wagner, D. Bauerschlag, M. P. Cooke, and G. M. Hampton, Exposing oncogenic dependencies for cancer drug target discovery and validation using RNAi, *Semin. Cancer Biol.* 2003 August; 13(4):293-300; J. S. Bedford and H. L. Liber, Applications of RNA interference for studies in DNA damage processing, genome stability, mutagenesis, and cancer, *Semin. Cancer Biol.* 2003 August; 13(4):301-8). In a similar way, an antisense approach might reduce the level of messenger produced by the I93M allele or any other that confers a decrease of the hydrolytic activity.

For targeted treatment with small interference RNAs (19-mer to 22-mer), specific sequences in the cDNA have to be selected for its use as anti-allele I93M or similar target. Using the oligonucleotide design software Tethys developed by Oryzon, a previous evaluation is performed to establish which is the oligonucleotide that has lower cross-hybridization potential with other expressed sequences present in the genome to reduce the probability that it may affect the expression of other genes. Also employing Tethys, it can be determined which is the most favorable position of the differential base in the oligo to maximize the effect of reduction of expression of the desired allele. Tethys is then used to evaluate which is the most favorable oligonucleotide length depending on the target sequence as shown in FIG. 6.

In the following table, some of the possible targets in the cDNA for reduction of expression of UCH-L1 I93M or of a UCH-L1 allele that does not contain the I93M mutation are described as an example.

```
UCH-L1 I93M    ggcacaatGggacttattc    (SEQ ID NO: 1)

UCH-L1 I93M    cacaatGggacttattcac    (SEQ ID NO: 2)

UCH-L1         ggcacaatCggacttattc    (SEQ ID NO: 3)

UCH-L1         cacaatCggacttattcac    (SEQ ID NO: 4)
```

It is also a part of the present invention to employ in vitro systems for analysis of therapeutic compounds and/or pharmaceutical compositions that may prevent neural damage produced by Lewy aggregates. Cell lines such as the SH-SY5Y neuroblastoma cell line, where treatments with 5-100 microM of MPP+, the active metabolite of MPTP, induce apoptosis in SH-SY5Y cells and reproduce the over-expression of α-synuclein that forms the Lewy aggregates characteristic of the DLB (C. Gomez-Santos, I. Ferrer, J. Reiriz, F. Vinals, M. Barrachina, and S. Ambrosio, MPP+ increases alpha-synuclein expression and ERK/MAP-kinase phosphorylation in human neuroblastoma SH-SY5Y cells, *Brain Res.* 2002 May 10; 935 (1-2):32-9). In these cell lines, efficiency of compounds can be verified by monitoring UCH-L1 levels, its enzymatic activities, deposits of α-synuclein and apoptosis of the cells. These therapeutic compounds and/or pharmaceutical compositions may bind the UCH-L1 protein and inhibit in a non-competitive manner the ubiquityl-ligase activity and restore its capacity to release normal ubiquitin. Alternatively, these therapeutic compounds and/or pharmaceutical compositions may modify expression of cell signaling pathways due to over-accumulation of proteins as a consequence of an alteration of the UPS system.

BRIEF DESCRIPTION OF THE FIGURES

FIG. 2A: levels of mRNA of UCH-L1 (mean±SEM) normalized with β-actin. FIG. 2B: levels of UCH-L1 protein (two bands of approximately 25 KDa), detected by Western blot in total homogenates of frontal cortex (area 8). β-actin (45 kDa) was detected as control of protein load. The image is representative of all the samples studied and indicated in Table I. FIG. 2C: Densitometric analysis of the UCH-L1 protein levels (mean±SEM) with the TotalLab v2.01 software. The protein levels of UCH-LI were normalized with those of β-actin. Values are statistically significant with *$p<0.05$ and **$p<0.01$ compared with control samples (ANOVA with the test post-hoc LSD).

FIG. 6 contains SEQ ID NOs:5-16, as represented sequentially from left to right (ATTCCTGTGGCACAATGGG (SEQ ID NO:5); TCCTGTGGCACAATGGGAC (SEQ ID NO:6); CTGTGGCACAATGGGACTT (SEQ ID NO:7); GTGGCACAATGGGACTTAT (SEQ ID NO:8); GGCACAATGGGACTTATTC (SEQ ID NO:9); CACAATGGGACTTATTCAC (SEQ ID NO:10); CAATGGGACTTATTCACGC (SEQ ID NO:11); ATGGGACTTATTCACGCAG (SEQ ID NO:12); GACTTATTCACGCAGCAGT (SEQ ID NO:13); CTTATTCACGCAGCAGTGG (SEQ ID NO:14); TATTCACGCAGCAGTGGCC (SEQ ID NO:15); and TTCACGCAGCAGTGGCCAA (SEQ ID NO:16)).

DESCRIPTION OF A PREFERRED EMBODIMENT

Figure 1A:
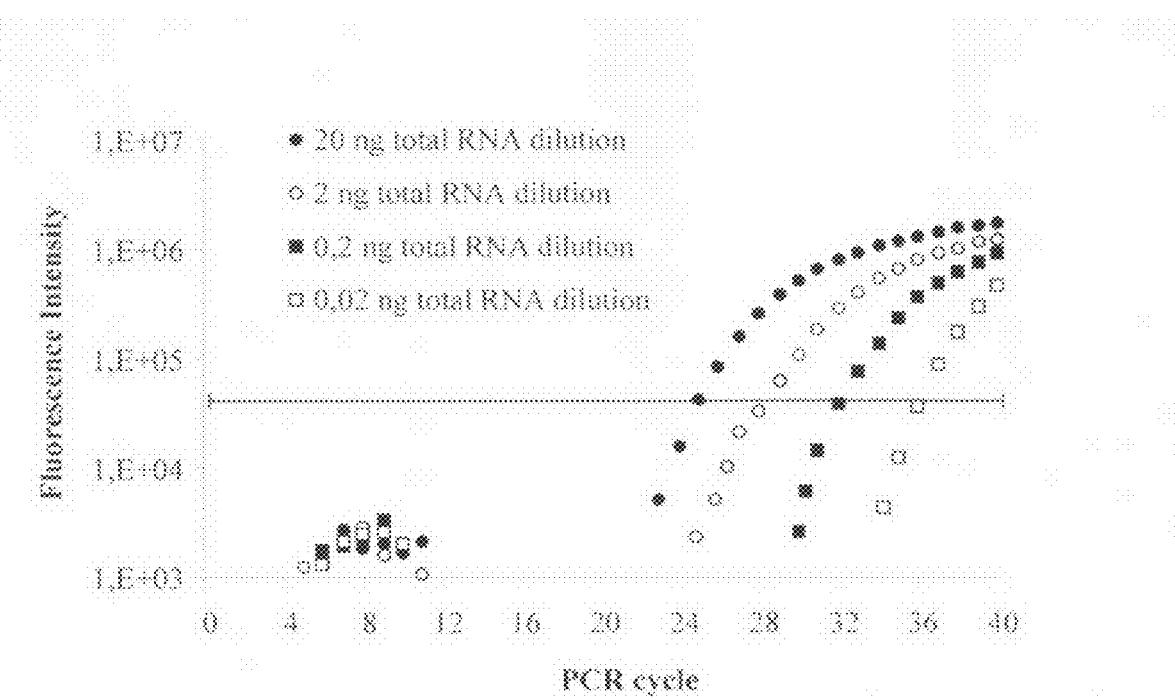
FIG. 1A: Graphical representation of UCH-L1 amplification through serial dilutions of RNA from cortical area 8 of the human brain. The horizontal line represents the threshold manually adjusted in the exponential phase. The intensity of fluorescence increases with the PCR cycles. The number of cycles from which the intensity of fluorescence exceeds the threshold line is defined as the threshold value CT on which the quantification is based.
Figure 1B:
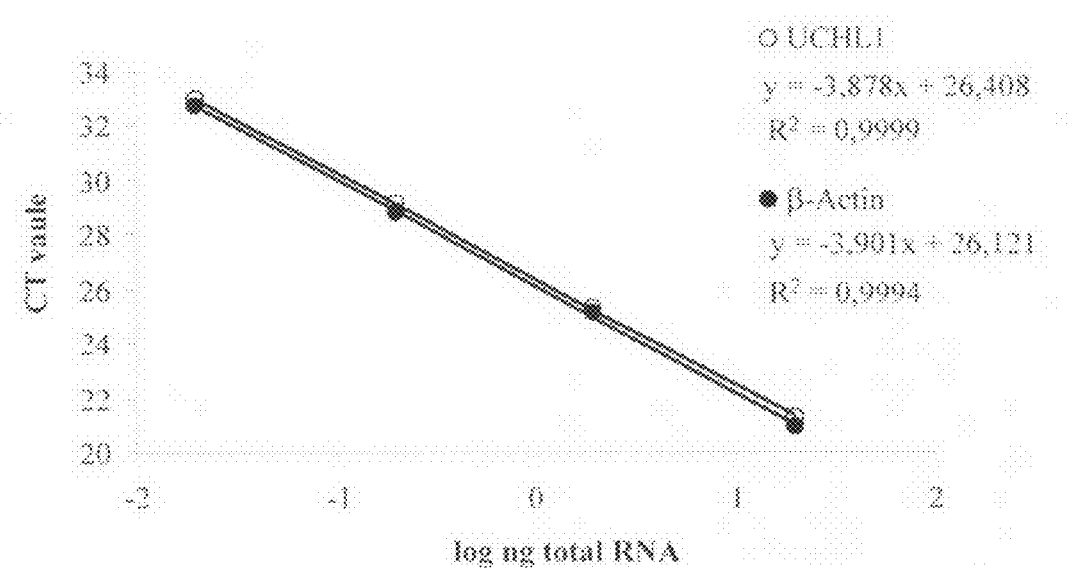
FIG. 1B: Representative standard curves for β-actin and UCH-L1 made from different concentrations of RNA from control human brain. The CT values (y axis) vs log of the different concentrations of RNA of control samples (x axis) show an inverse linear correlation.
Figure 2A:
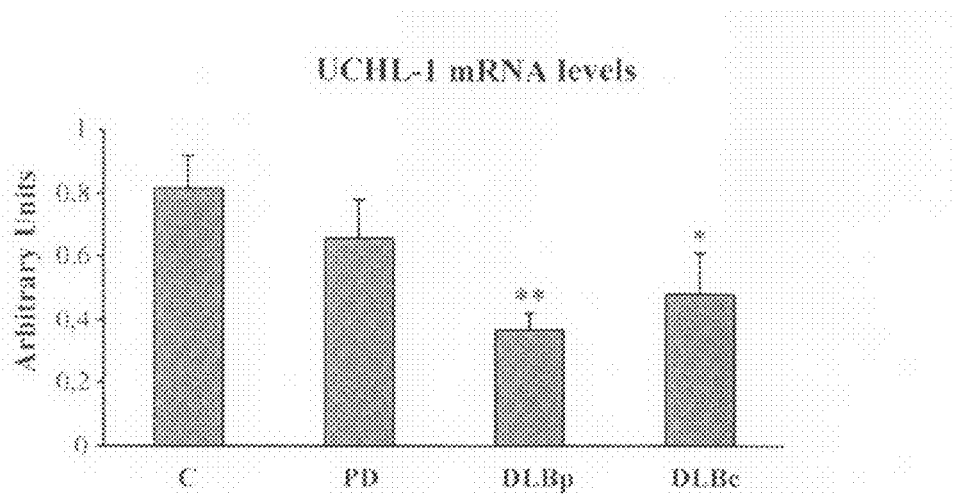
FIGS. 2A-2C: Relative expression levels of the UCH-L1 gene in the frontal cortex of controls (C, n=6), Parkinson's disease (PD, n=6), diffuse Lewy body disease, dementia with Lewy bodies, pure form (DLBp, n=7) and common form (DLBc, n=6).
Figure 2B:
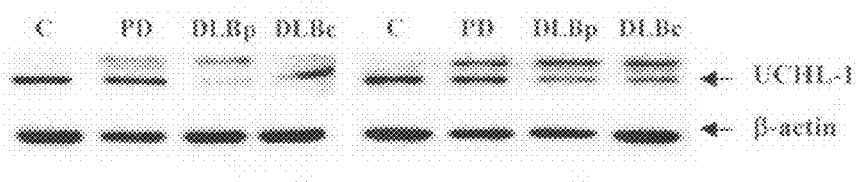
Figure 2C:
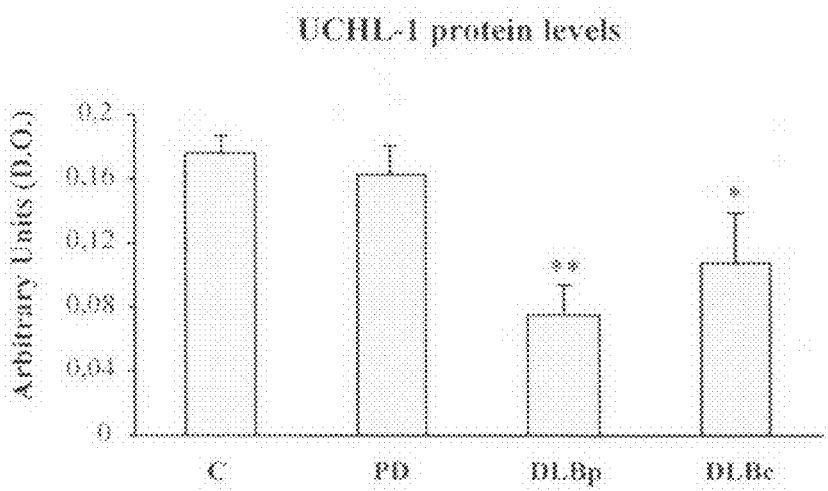
Figure 3:
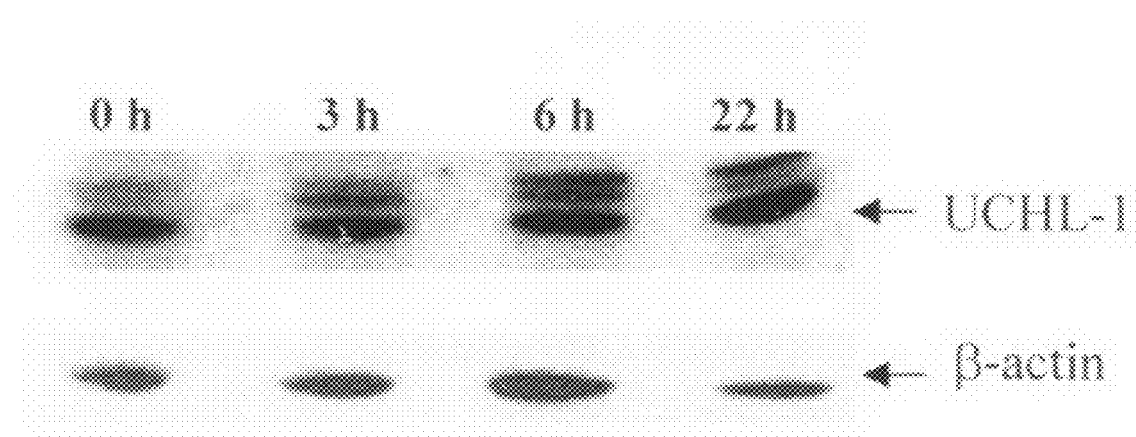
FIG. 3: Post-mortem stability of the UCH-L1 protein levels (two bands of approximately 25 kDa) detected by Western blot in total homogenates of frontal cortex of an individual sample (3 hours post-mortem). Samples were immediately frozen in liquid nitrogen (0 hour) or left at room temperature for 3, 6 or 22 hours and then frozen in liquid nitrogen. There is no apparent degradation of UCH-L1 until 22 hours.

Following is the description of a preferred embodiment, although non-limiting, of the invention.

In the following table are summarized cases studied in the present series along with corresponding neuropathological data: Parkinson's disease (PD), dementia with Lewy bodies in pure form (DLBp) and in common form (DLBc), and controls. M=male; F=female; NFT=neurofibrillary tangle. Braak stages indicate the changes of Alzheimer's disease (AD) associated with DDLB described by Braak and Braak (H. Braak and E. Braak (1999), Temporal sequence of Alzheimer's disease-related pathology, In: *Cerebral Cortex*, vol 14, Neurodegenerative and age-related changes in structure and function of cerebral cortex (A. Peters and J. H. Morrison, eds), pp. 475-512, New York, Boston, Dordrecht, London, Moscow: Kluwer Academic/Plenum Publishers).

| Case | disease | Genre | Age (y) | Post-mortem (h) | Braak stage βA4 amyloid | NFT |
|---|---|---|---|---|---|---|
| 1 | Control | M | 63 | 17 | 0 | 0 |
| 2 | Control | M | 70 | 13 | 0 | 0 |
| 3 | Control | M | 79 | 7 | 0 | II |
| 4 | Control | F | 65 | 4 | 0 | I |
| 5 | Control | F | 80 | 21 | 0 | I |
| 6 | Control | F | 82 | 11 | A | III |
| 7 | PD | M | 66 | 5 | 0 | I |
| 8 | PD | M | 81 | 5 | A | II |
| 9 | PD | M | 88 | 2 | 0 | II |
| 10 | PD | M | 70 | 19 | 0 | 0 |
| 11 | PD | F | 60 | 4 | A | 0 |
| 12 | PD | F | 70 | 4 | 0 | 0 |
| 13 | DLBp | M | 60 | 8 | A | I |
| 14 | DLBp | M | 68 | 12 | B | 0 |
| 15 | DLBp | M | 71 | 6 | B | 0 |
| 16 | DLBp | M | 81 | 16 | A | I |
| 17 | DLBp | M | 85 | 7 | B | II |
| 18 | DLBp | F | 70 | 8 | 0 | 0 |
| 19 | DLBp | F | 77 | 5 | B | 0 |
| 20 | DLBc | M | 78 | 6 | C | V |
| 21 | DLBc | M | 78 | 7 | C | V |
| 22 | DLBc | F | 71 | 5 | C | V |
| 23 | DLBc | F | 78 | 7 | C | VI |
| 24 | DLBc | F | 78 | 13 | C | IV |
| 25 | DLBc | F | 91 | 5 | C | V |

RNA and protein samples were isolated from the patients with ethical permission as described below.

Isolation of mRNA from the samples of cortical area 8 from the different patients and controls: mRNA was isolated in two steps. Total RNA was obtained using the TRizol reagent (Life Technologies) and then mRNA free of transfer RNA and 5S and 5.8S ribosomal RNA was obtained using the kit RNEASY® Protect Mini Kit (Qiagen). Frozen human brain tissue was homogenized directly in 1 ml of TRizol per 100 mg of tissue, and total RNA extracted according to the protocol of the manufacturer. Purified total RNA was resuspended in 100 μl of RNase-free water and the purification of the mRNA was performed according to the specifications indicated in the RNEASY® Protect Mini Kit with minor changes; DNase I treatment was not performed since the genomic DNA was removed during the extraction with TRizol. The concentration of each sample was measured by absorbance at 260 nm, and the RNA integrity was confirmed by agarose-formaldehyde gels electrophoresis.

DNA arrays: For the transcriptomic analysis, RNA samples were additionally analysed using the Agilent 2100 BioAnalyzer, which calculates fragment size and concentration of the sample as well as the ratio between the signals of the 16S and 28S RNA. All the samples were labeled with the Kit MessageAmp RNA (Ambion). First-strand cDNA synthesis was primed using oligo-dT primers. Samples of labeled RNA were analyzed in oligo DNA chips representing 627 genes of specific interest, each one represented by two sets of five oligos randomly distributed on the surface of the DNA chip. The oligos were synthesized using a Geniom I benchtop DNA-chip synthesis apparatus from FEBIT, a microarray platform that integrates all functions in a single instrument (M. Baum, S. Bielau, N. Rittner, K. Schmid, K. Eggelbusch, M. Dahms, A. Schlauersbach, H. Tahedi, M. Beier, R. Guimil, M. Scheffler, C. Hermann, J. M. Funk, A. Wixmerten, H. Rebscher, M. Honig, C. Andreae, D. Buchner, E. Moschel, A. Glathe, E. Jager, M. Thom, A. Greil, F. Bestvater, F. Obermeier, J. Burgmaier, K. Thome, S. Weichert, S. Hein, T. Binnewies, V. Foitzik, M. Muller, C. F. Stahler, and P. F. Stahler, Validation of a novel, fully integrated and flexible microarray benchtop facility for gene expression profiling, *Nucleic Acids Res.* 2003; 31:e151). Raw data were normalized with the non-linear method of Lowess (C. Workman, L. J. Jensen, H. Jarmer, R. Berka, L. Gautier, H. B. Nielser, H. H. Saxild, C. Nielsen, S. Brunak, and S. Knudsen, A new non-linear normalization method for reducing variability in DNA microarray experiments, *Genome Biol.* 2002; 3:9).

In these experiments, we established a cut-off of 0.75-fold change for repressed genes and 1.5 for overexpressed genes in DLB versus controls. We obtained one overexpressed gene and 16 repressed genes, several of them involved in the UPS degradation pathway and, to a significant extent, the UCH-L1. Complementary techniques were used to confirm this variation.

Synthesis of the cDNA and PCR Taqman: 200 ng of human RNA (in 3.85 μl of water) in each 10 μl of reverse transcription reaction were mixed with 2.5 μM of oligo-dT primer, 1×RT TaqMan buffer, 5.5 mM $MgCl_2$, 500 μM of each dATP, dTTP, dCTP and dGTP, 0.08 U RNase inhibitor and 0.31 U of the reverse transcriptase MultiScribe (Applied Biosystems). Reactions were performed at 25° C. for 10 minutes to maximize the primer-RNA template union, followed by incubation at 48° C. for 30 minutes, and inactivation of the reverse transcriptase at 95° C. for 5 minutes. Parallel reactions were performed in absence of the reverse transcriptase MultiScribe to ensure the absence of contaminant genomic DNA. The TaqMan probe (Applied Biosystems) anneals to one of the template DNA strands between forward and reverse PCR primers. It contains a fluorophore, which is hydrolized by the Taqpolymerase, the amount of liberated fluorophore being proportional to the amount of product generated in the PCR reaction. Primers and the probes specific for human UCH-L1 and β-actin genes were obtained as Assays-on-Demand from Applied Biosystems. Human β-actin was used as endogenous control.

TaqMan PCR assays for the UCH-L1 and the endogenous control β-actin were performed in triplicate on cDNA samples in 96-well optical plates using the thermocycler ABI Prism 7700-Sequence Detection system (PE Applied Biosystems). The plate was covered with optical strips (Applied Biosystems). In each 20 μl TaqMan reaction, 9 μl of cDNA (dilution 1/50, which corresponds approximately to the cDNA obtained from 4 ng of RNA) were mixed with 1 μl of 20× TaqMan probe and 10 μl of 2× TaqMan Universal PCR Master Mix (Applied Biosystems). For control and normalization purposes, parallel assays were performed for each sample with the β-actin primers and probe. The reaction was carried out by incubation as follows: 50° C. for 2 minutes, 95° C. for 10 minutes, and 40 cycles at 95° C. for 15 seconds, 60° C. for 1 minute. Standard curves for UCH-L1 and β-actin were prepared using serial dilutions of RNA converted to cDNA from control human brain. Finally, all data from TaqMan PCR were collected with the Sequence Detector Software (SDS version 1.9; Applied Biosystems).

Figure 4:
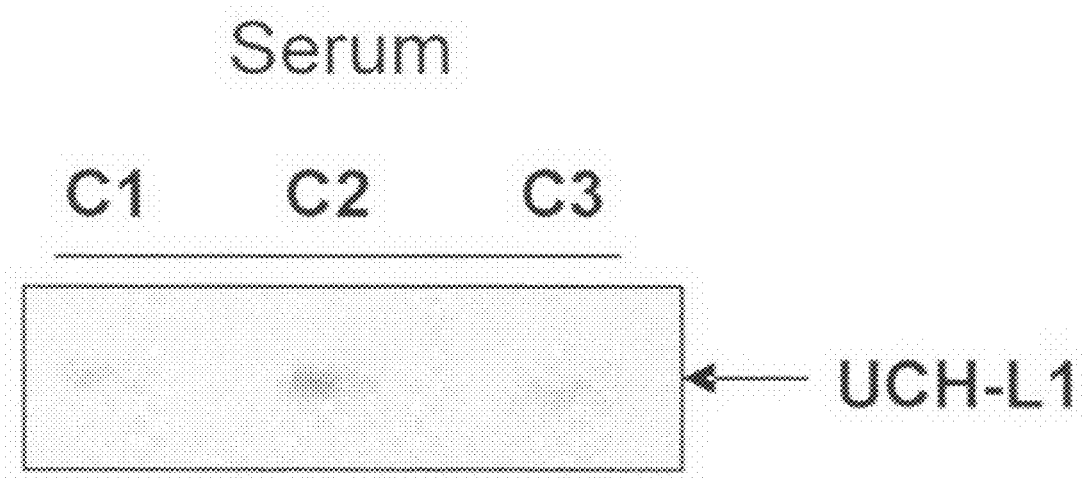
FIG. 4: UCH-L1 protein levels detected by Western blot in serum of control subjects. The image shows a specific band corresponding to the apparent molecular weight of UCH-L1.
Figure 5:
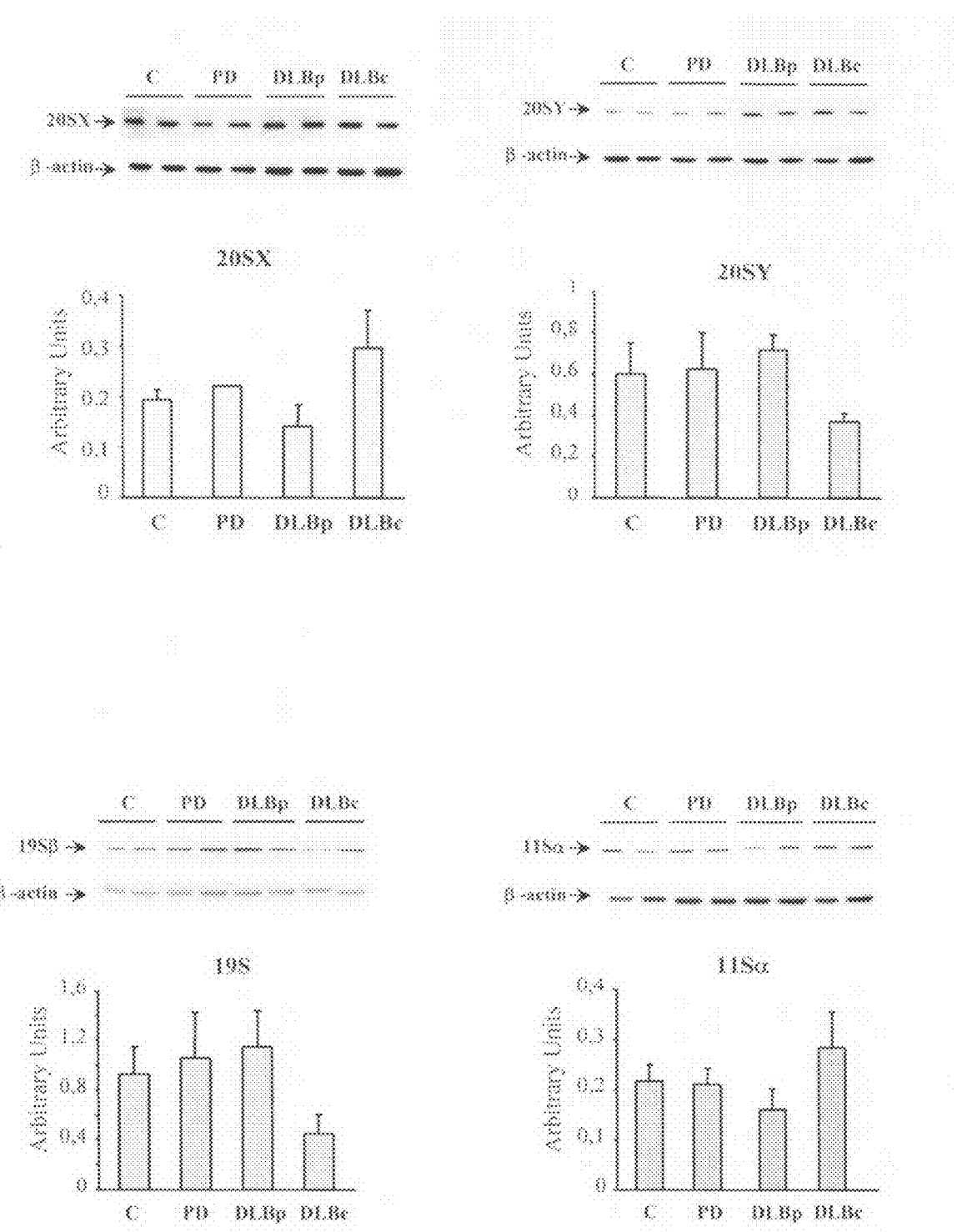
FIG. 5: Protein levels of the subunits of the proteosome in the frontal cortex of controls (C, n=6), Parkinson's disease (PD, n=6), diffuse Lewy body disease, dementia with Lewy bodies, pure form (DLBp, n=7) and common form (DLBc, n=6): subunits β of the 20S complex, 20SX and 20SY, 19S complex and the 11Sα activator. β-actin used as control. The image is representative of all the samples indicated in Table I. Densitometric analysis of the protein levels of the subunits of the proteosome (mean±SEM) using the TotalLab v2.01 software. The UCH-L1 protein values were normalized with those of β-actin. No statistically significant differences were detected between controls and pathological cases.
Figure 6:
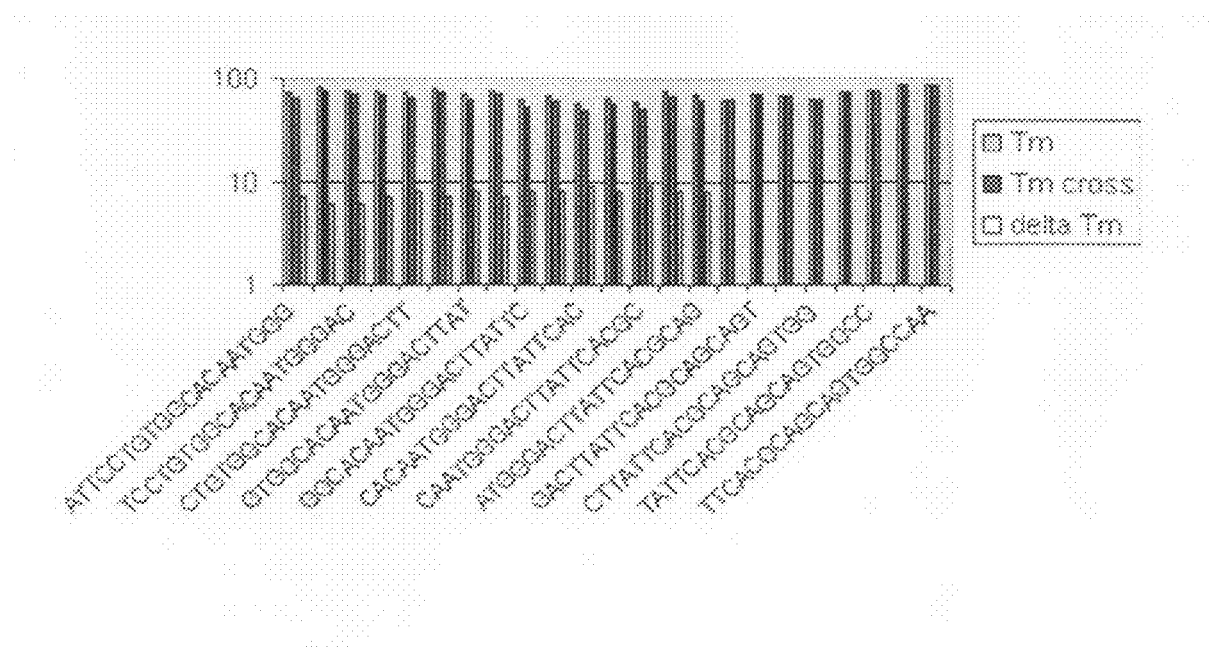
FIG. 6: Temperatures of hybridization and cross-hybridization of oligonucleotides specifically designed to amplify the specific allele I93M of UCH-L1 compared to the values of the oligos that are complementary of the normal allele. Tm: temperature of hybridization of the oligo specific for the UCH-L1 I93M gene with its complementary oligo. Tm cross: temperature of hybridization of the oligo specific for the UCH-L1 I93M gene with the complementary oligo for the wild-type UCH-L1 gene. Delta Tm: Tm-Tm cross.

Electrophoresis and Western blotting: To check if UCH-L1 protein levels were decreased, samples of frozen frontal cortex (100 mg) were directly homogenized in 1 ml of lysis buffer (20 mM Hepes, 10 mM KCl, 1.5 mM $MgCl_2$, 1 mM EDTA, 1 mM EGTA, 1 mM DDT, 2 mM PMSF, 1 μg/ml aprotinin, leupeptin and pepstatin) and sonicated. Lysates were centrifuged at 5,000 rpm for 10 minutes at 4° C. and the protein concentration was determined by the BCA method (Pierce). 50 μg of total protein were heated to 95° C. for 3 minutes and loaded on SDS-polyacrylamide gels with Tris-glycine buffer. Proteins were separated by gel electrophoresis using the mini-protean system (Bio-Rad) and transferred to nitrocellulose membranes (Bio-Rad) with a Trans-Blot SD Semi-Dry Transfer Cell (Bio-Rad) for 45 minutes at 40 mA. Nitrocellulose membranes were blocked with TWEEN® 20 TBS (TBST) containing 5% fat-free milk for 30 minutes. Subsequently, membranes were incubated at 4° C. overnight with the corresponding primary antibody prepared in TBST buffer containing 3% of BSA. Antibodies used were: anti-UCH-L1 (AB5937, Chemicon), anti-UCH-L1 (MCA-2084, Serotec), anti-β-actin (clone AC-74, Sigma), anti-19S 1β proteosome (PA1-973, Affinity BioReagents), anti-11Sα proteosome activator (PA1-960, Affinity BioReagents), anti-20SX proteosome (PA1-977, Affinity BioReagents) and anti-20SY proteosome (PA1-978, Affinity BioReagents). Antibodies were used at a dilution of 1:500. Following incubation with the primary antibody, membranes were washed three times with TBST buffer for 5 minutes at room temperature, and then incubated with the corresponding secondary antibody, IgG labeled with peroxidase (Dako) at a dilution 1:1,000 (1:5,000 for β-actin) for 1 hour at room temperature. Then membranes were washed four times for 5 minutes with TBST buffer at room temperature and developed with the chemoluminenscence ECL Western blotting system (Amersham/Pharmacia) followed by the exposure of autoradiographic film (Hyperfilm ECL, Amersham). Quantification of UCH-L1 levels may be done in peripheral tissue such as serum or cerebrospinal fluid. As shown in FIG. 4, endogenous UCH-L1 levels can be detected in these biological fluids.

Quantitative analysis of the data: Densitometric quantification of the Western blot bands was performed with the TotalLab v2.01 software. For statistical analysis Statgraphics Plus v5 software was used.

The invention claimed is:

1. A method of diagnosing dementia with Lewy bodies (DLB) in a subject, the method comprising:
   obtaining a sample from the subject's frontal cortex; and
   analyzing the level of expression of ubiquitin carboxy-terminal hydrolase L1 (UCH-L1) gene in the sample, wherein reduced levels of expression of UCH-L1 gene compared to controls is diagnostic of DLB, as determined by comparing the level of expression of UCH-L1 gene in the sample to UCH-L1 gene expression levels in Alzheimer's Disease (AD) and Parkinson's disease (PD).

* * * * *

SEQUENCE LISTING

<160> NUMBER OF SEQ ID NOS: 16

<210> SEQ ID NO 1
<211> LENGTH: 19
<212> TYPE: DNA
<213> ORGANISM: Artificial
<220> FEATURE:
<223> OTHER INFORMATION: chemically synthesized

<400> SEQUENCE: 1
ggcacaatgg gacttattc                                            19

<210> SEQ ID NO 2
<211> LENGTH: 19
<212> TYPE: DNA
<213> ORGANISM: Artificial
<220> FEATURE:
<223> OTHER INFORMATION: chemically synthesized

<400> SEQUENCE: 2
cacaatggga cttattcac                                            19

```
<210> SEQ ID NO 3
<211> LENGTH: 19
<212> TYPE: DNA
<213> ORGANISM: Artificial
<220> FEATURE:
<223> OTHER INFORMATION: chemically synthesized

<400> SEQUENCE: 3
ggcacaatcg gacttattc                                                    19

<210> SEQ ID NO 4
<211> LENGTH: 19
<212> TYPE: DNA
<213> ORGANISM: Artificial
<220> FEATURE:
<223> OTHER INFORMATION: chemically synthesized

<400> SEQUENCE: 4
cacaatcgga cttattcac                                                    19

<210> SEQ ID NO 5
<211> LENGTH: 19
<212> TYPE: DNA
<213> ORGANISM: Artificial
<220> FEATURE:
<223> OTHER INFORMATION: chemically synthesized

<400> SEQUENCE: 5
attcctgtgg cacaatggg                                                    19

<210> SEQ ID NO 6
<211> LENGTH: 19
<212> TYPE: DNA
<213> ORGANISM: Artificial
<220> FEATURE:
<223> OTHER INFORMATION: chemically synthesized

<400> SEQUENCE: 6
tcctgtggca caatgggac                                                    19

<210> SEQ ID NO 7
<211> LENGTH: 19
<212> TYPE: DNA
<213> ORGANISM: Artificial
<220> FEATURE:
<223> OTHER INFORMATION: chemically synthesized

<400> SEQUENCE: 7
ctgtggcaca atgggactt                                                    19

<210> SEQ ID NO 8
<211> LENGTH: 19
<212> TYPE: DNA
<213> ORGANISM: Artificial
<220> FEATURE:
<223> OTHER INFORMATION: chemically synthesized

<400> SEQUENCE: 8
gtggcacaat gggacttat                                                    19

<210> SEQ ID NO 9
<211> LENGTH: 19
<212> TYPE: DNA
<213> ORGANISM: Artificial
<220> FEATURE:
<223> OTHER INFORMATION: chemically synthesized
```

<400> SEQUENCE: 9
ggcacaatgg gacttattc					19

<210> SEQ ID NO 10
<211> LENGTH: 19
<212> TYPE: DNA
<213> ORGANISM: Artificial
<220> FEATURE:
<223> OTHER INFORMATION: chemically synthesized

<400> SEQUENCE: 10
cacaatggga cttattcac					19

<210> SEQ ID NO 11
<211> LENGTH: 19
<212> TYPE: DNA
<213> ORGANISM: Artificial
<220> FEATURE:
<223> OTHER INFORMATION: chemically synthesized

<400> SEQUENCE: 11
caatgggact tattcacgc					19

<210> SEQ ID NO 12
<211> LENGTH: 19
<212> TYPE: DNA
<213> ORGANISM: Artificial
<220> FEATURE:
<223> OTHER INFORMATION: chemically synthesized

<400> SEQUENCE: 12
atgggactta ttcacgcag					19

<210> SEQ ID NO 13
<211> LENGTH: 19
<212> TYPE: DNA
<213> ORGANISM: Artificial
<220> FEATURE:
<223> OTHER INFORMATION: chemically synthesized

<400> SEQUENCE: 13
gacttattca cgcagcagt					19

<210> SEQ ID NO 14
<211> LENGTH: 19
<212> TYPE: DNA
<213> ORGANISM: Artificial
<220> FEATURE:
<223> OTHER INFORMATION: chemically synthesized

<400> SEQUENCE: 14
cttattcacg cagcagtgg					19

<210> SEQ ID NO 15
<211> LENGTH: 19
<212> TYPE: DNA
<213> ORGANISM: Artificial
<220> FEATURE:
<223> OTHER INFORMATION: chemically synthesized

<400> SEQUENCE: 15
tattcacgca gcagtggcc					19

<210> SEQ ID NO 16

```
<211> LENGTH: 19
<212> TYPE: DNA
<213> ORGANISM: Artificial
<220> FEATURE:
<223> OTHER INFORMATION: chemically synthesized

<400> SEQUENCE: 16
ttcacgcagc agtggccaa                                                    19
```